US008528426B2

(12) United States Patent
Burke

(10) Patent No.: US 8,528,426 B2
(45) Date of Patent: Sep. 10, 2013

(54) DEVICE FOR TRANSFER OF BODY FLUIDS

(75) Inventor: Craig Andrew Burke, Cremorne (AU)

(73) Assignee: Noble House Group Pty. Ltd. (AU)

( * ) Notice: Subject to any disclaimer, the term of this patent is extended or adjusted under 35 U.S.C. 154(b) by 2 days.

(21) Appl. No.: 13/120,162

(22) PCT Filed: Sep. 23, 2009

(86) PCT No.: PCT/AU2009/001263
§ 371 (c)(1),
(2), (4) Date: Mar. 22, 2011

(87) PCT Pub. No.: WO2010/034058
PCT Pub. Date: Apr. 1, 2010

(65) Prior Publication Data
US 2011/0174089 A1   Jul. 21, 2011

(30) Foreign Application Priority Data
Sep. 23, 2008   (AU) .................................. 2008904934

(51) Int. Cl.
*G01N 1/10* (2006.01)
(52) U.S. Cl.
USPC ....................................................... 73/864.74

(58) Field of Classification Search
None
See application file for complete search history.

(56) References Cited

U.S. PATENT DOCUMENTS

| 4,939,940 | A  | * | 7/1990  | Tsukida .................... 73/864.74 |
|-----------|----|---|---------|----------------------------------------|
| 4,976,925 | A  | * | 12/1990 | Porcher et al. ................ 422/501 |
| 5,270,219 | A  | * | 12/1993 | DeCastro et al. ............. 436/180 |
| 6,217,560 | B1 | * | 4/2001  | Ritger et al. .................. 604/243 |
| 6,656,433 | B2 | * | 12/2003 | Sasso ............................ 422/569 |
| 6,821,267 | B2 | * | 11/2004 | Veillon et al. ................. 604/192 |
| 7,082,848 | B2 | * | 8/2006  | Fjerdingstad .............. 73/863.85 |

FOREIGN PATENT DOCUMENTS

| EP | 0982006       | 12/2005 |
| JP | 2110-262628   | 9/2000  |
| JP | 2005-152504   | 6/2005  |
| WO | WO 01/05210   | 1/2001  |

* cited by examiner

*Primary Examiner* — Robert R Raevis
(74) *Attorney, Agent, or Firm* — Galbreath Law Offices, P.C.; John A. Galbreath

(57) ABSTRACT

A cannula (10) for use in removing samples of fluid from a container sealed with a pierceable membrane, the cannula including a hollow needle like portion (12) having a pointed forward end (20) shaped to allow forcible penetration through the membrane, the rear end (14) having a first bore (26) and an insert (40) located within the first bore (40) that reduces the effective size of the first bore (26) without blocking the first bore (26).

20 Claims, 4 Drawing Sheets

EXHIBIT 1

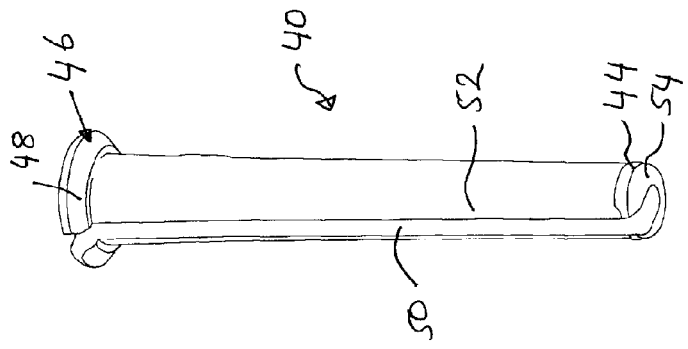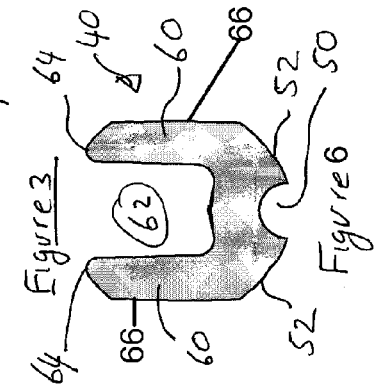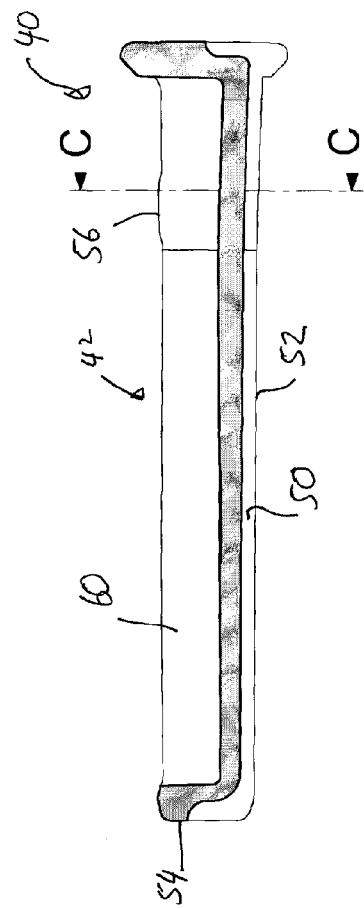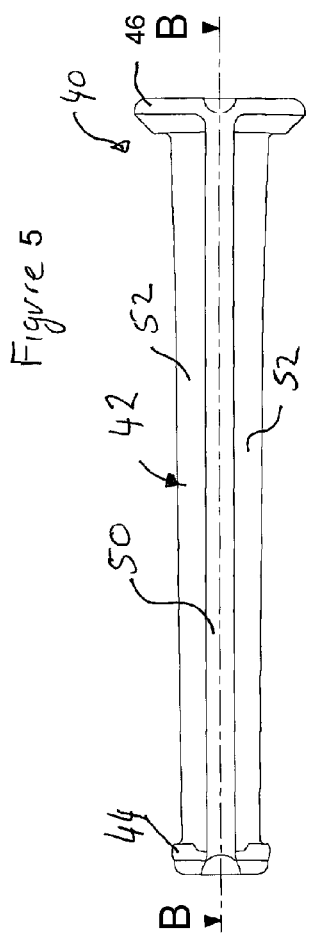

DEVICE FOR TRANSFER OF BODY FLUIDS

FIELD OF INVENTION

This invention relates to testing of samples of fluids and more particularly culture samples used for testing for bacterial contamination of blood. However the invention is not limited to such uses.

BACKGROUND

Blood and other body samples are frequently collected in small vials or test tubes for subsequent testing. Blood is also collected during blood donation in donation bags. The vials, tubes or bags are sealed to prevent contamination. Testing of the blood typically involves removing, in a sterile manner, a small amount of the blood from the relevant container and, typically, placing a drop onto each of a number of test media. The media may be absorbent paper, a slide or any suitable media. In addition blood in blood donation bags is tested for bacterial contamination. This typically involves placing a small amount of blood from the donation bag in a container having a liquid medium in which bacteria may grow. After some time some of the medium is removed and placed on test media. These containers are commonly referred to as culture bottles.

One common collection vial used is the evacuated tube. Such a tube is, in effect, a sample tube with its open end sealed by a rubber membrane. The tube is supplied at a low pressure and blood or other fluids are introduced by passing a sterile cannula or the like connected to a source of blood (such as a patient, blood donor or blood bag) through the membrane into the interior of the tube. The low pressure assists in drawing blood into the tube. Culture bottles are similar, albeit larger and not being evacuated, in being rigid and having a pierceable membrane sealing an opening.

Removal of a sample of fluid typically involves passing a cannula through the membrane and inverting the vial or bottle. The fluid may be draw out of the container using gravity alone or by connecting the cannula to a syringe and using the syringe to draw the fluid out. Because the vials and bottles are usually rigid, removal of fluid reduces the pressure within and tends to inhibit removal of fluid.

A typical cannula used may be a simple syringe needle having a hollow metal shaft with a pointed end. The interior diameter of the needle is relatively small (about 0.4 mm). A drop of fluid from such a bore typically forms a circle of about 5 to 7 mm diameter when dropped onto typical test media, such as absorbent paper.

Because the bore has a small diameter the amount of fluid required to fill the needle is small and so filling the needle does not reduce the pressure within the vial to a significant amount. This results in the ability to easily remove the necessary number of fluid drops and the fluid flows easily and gives drops of consistent size.

Due to the risk of needle stick injuries the use of metal needles and the like is discouraged.

Cannulas formed of plastics or other polymers have been proposed for other uses. Whilst these have a pointed end, due to the nature of the plastics material they are not considered to be a needle stick risk. However, cannulas formed of plastics cannot be manufactured in a cost effective manner with a passageway with a small diameter corresponding to that of a metal cannula and, typically, are manufactured with a bore diameter of 1 mm or greater. This results in a significantly greater volume of the bore. Attempting to use a plastics cannula with such a large diameter bore to withdraw fluid from a sealed container is not successful and only one or two drops can be obtained before the reduced pressure caused by withdrawing fluid to fill the cannula prevents or limits further withdrawal. In addition, a drop of fluid from a bore of such a cannula is typically unnecessarily large.

SUMMARY OF THE INVENTION

In one broad form the invention provides a medical device having an internal bore through which fluid may pass and an insert located in the bore that reduces the effective volume of the bore.

The invention may also comprise apparatus for use in removing samples of fluid from a container sealed with a pierceable membrane, the apparatus including a plastics cannula having a hollow pointed forward end shaped to allow forcible penetration through the membrane, the rear end having a first bore of a first diameter and an insert located within the first bore that reduces the effective size of the first bore.

The hollow pointed forward end preferably has a second bore coaxial with the first bore.

In another broad form the invention provides a plastics cannula for use in removing samples of fluid from a container sealed with a pierceable membrane, the cannula including
  an elongate body having a front end and a rear end;
  a first bore extending from the rear of the body toward the front end;
  a small diameter needle like portion extending from the front end of the body having a pointed forward end shaped to allow forcible penetration through the membrane and having a second bore therein that extends from the forward end through the front end of the body to be in fluid communication with the first bore;
  the cross-section area of the first bore being significantly greater than that of the second bore, and
an insert located within the first bore and extending from the front end of the first bore to the rear end to define a passageway from the second bore to the rear of the body formed between an outer surface of the insert and a surface of the first bore wherein the passageway has a significantly smaller volume than the first bore.

Preferably the first bore has a rear portion adapted to receive a male lure fitting.

The first bore may have a forward portion. The forward portion may be a continuation of the rear portion.

The forward portion, in cross section, may have an area equivalent to a circle of diameter in the range of 1 to 10 mm, preferably in the range of 3 to 5 mm.

Preferably the forward and rear portions are frusto-conical, diverging to the rear, but may be cylindrical. The first bore need not be circular in cross section.

In the preferred embodiment the first bore is between about 15 and 30 mm long, more preferably about 26 mm long and has a diameter that ranges from 3.5 mm to 4.2 mm.

The second bore is preferably between about 15 and 30 mm long, more preferably about 20 mm long with an inside diameter of about 1 mm.

The insert may substantially fill the first bore in cross section. Preferably the insert has a surface that engages a portion of the inside of the first bore. The surface has a longitudinally extending recess that, with a part of the surface of the first bore, defines a passageway. In the preferred embodiment this passageway has an area or a flow rate for fluid equivalent to a metal passageway of about 0.4 mm in inside diameter.

The recess preferably extends radially inwards on the inner end surface of the insert.

The insert preferably extends the full length of the first bore and extends out of the free end of the first bore. Preferably the exposed end of the insert has a head larger than the end of the first bore. The head preferably has a frusto-conical surface that engages the end of the bore.

Preferably the inset is an interference fit within the bore and may be removed by the user. Preferably the inner end of the insert is an interference fit with the inner end of the first bore. Other parts of the insert may also be an interference fit with the first bore.

The invention shall be better understood from the drawings and following non-limiting description of preferred embodiments of the invention.

BRIEF DESCRIPTION OF THE DRAWINGS

FIG. 3 is a perspective view of a component of the device of FIG. 1.
FIG. 4 is a side view of the component of FIG. 3.
FIG. 5 is a longitudinal cross sectional view of the component of FIG. 3 taken along line BB of FIG. 4.
FIG. 6 is an axial cross sectional view of the component of FIG. 3 taken along line CC of FIG. 5.

DETAILED DESCRIPTION OF PREFERRED AND OTHER EMBODIMENTS

Figure 2:
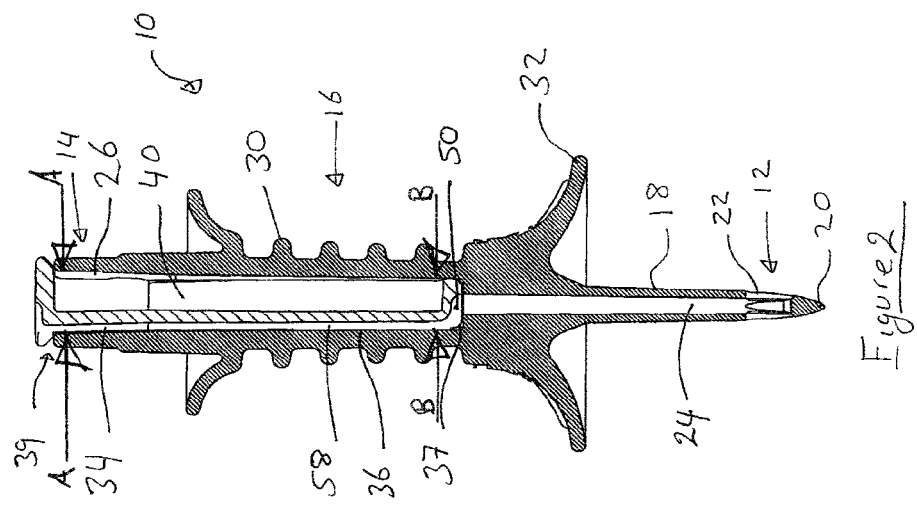
FIG. 2 is an axial cross section of the device of FIG. 1 taken along line AA of FIG. 1.
Figure 1:
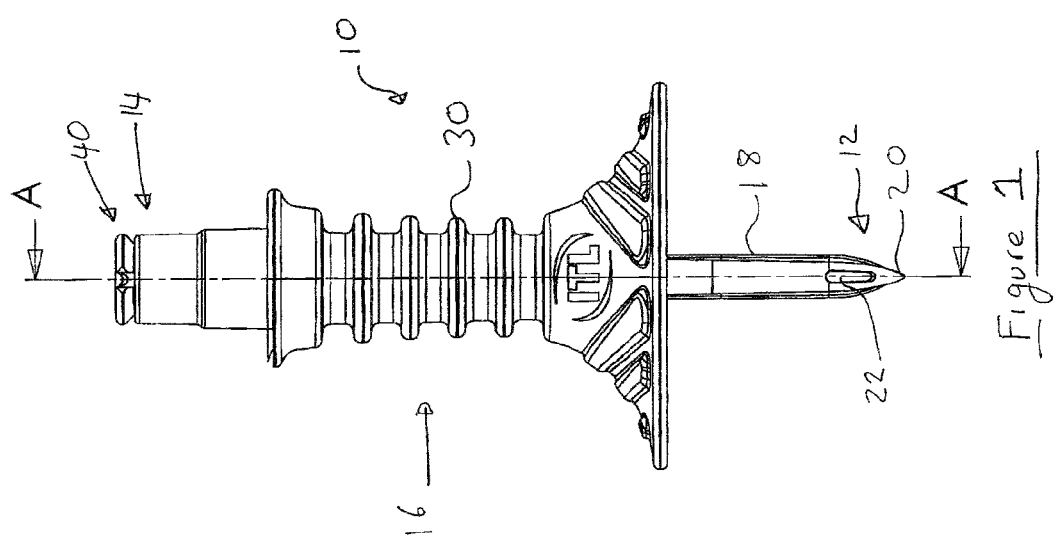
FIG. 1 is a side view of an embodiment of the invention.

Referring to the drawings there is shown a blunt-tip cannula 10 that comprises one example of the invention. The cannula 10 is formed as a plastic moulding with a forward end 12, a rear end 14 and a body 16. The forward end 12 is formed as a hollow integral small diameter needle-like tube 18 extending from the front of the body. Small diameter needle-like tube 18 has a pointed tip 20 which has side apertures 22 that communicate with small diameter inner second bore 24. Because the cannula is formed of plastics material the tip 20 is not classified as presenting a needle stick injury risk.

The second bore 24 is approximately 20 mm long and has an internal diameter of approximately 1 mm at the end adjacent the tip 20. For manufacturing reasons the bore is slightly tapered, diverging at about 1 degree toward the rear end. In combination with the length of about 20 mm, this diameter is generally the smallest that currently can be economically manufactured using plastics injection moulding methods.

The rear end 14 of the cannula is also tubular but with a first bore 26 of much larger diameter than second bore 24 of the forward end 12. The second bore 24 and first bore 26 present a single passageway 25 such that fluid entering the first bore 24 via openings 22 may pass along the passageway and exit the rear end of bore 26.

The body 16 is provided with deep ribs or grooves 30 to provide a finger grip and has a flared skirt 32 at its forward end that forms a finger stop which inhibits the fingers of a user (not shown) from slipping forward under the force of inserting tip 20 into a vial or culture bottle. The outside configuration is not critical to the working of the invention.

The first bore 26 has a rear portion 34 and a forward portion 36. The rear portion 34 is adapted to receive a conventional male luer fitting, such as found on the end of a conventional syringe. Consequently, the rear portion 34 diverges toward the free end of the bore. Provision of the divergent luer fitting is not essential and may be omitted. The rear portion 34 may be of constant diameter.

The forward portion 36 may be a continuation of the rear portion 34, with a divergent bore, be a bore of constant diameter or it may be different to the rear portion. In the preferred embodiment both the rear and forward portions 34, 36 diverge toward the rear end.

The first bore 26 has a diameter that ranges from about 3.5 mm at its base 37 to 4.2 mm at its opening 39 and in the preferred embodiment is about 26.5 mm long.

Located within the first bore 26 is a reducing plug or insert 40. This insert 40 has a central portion 42 and forward and rear heads 44 and 46 respectively.

The insert 40 is configured so that when fully inserted into the first bore 26 the forward head 44 bears against the end 37 of the first bore 26 whilst the rear head 46 rests on the end 39 of the first bore 26. The head 46 has an angled surface 48 that engages the end 39.

The insert 40 has a longitudinally extending surface 52 that corresponds to the inner surface of the first bore 26. As seen in FIG. 2, when located within the first bore this surface 52 engages the inner surface of the first bore 26.

A recess 50 extends longitudinally along the surface 52 between the forward and rear heads 44, 46. This recess 50 is generally semicircular and has a diameter of approximately 0.5 mm. The recess 50 extends generally radially inwards in the end surface 54 of forward head 44 to the centre of the head.

As seen in FIG. 2, when the insert is in the first bore the recess 50 overlies the opening of the second bore 24 into the first bore 26.

The forward head 44 is an interference fit in the end of the first bore 26 and so substantially blocks the first bore. The insert also has a portion 56 near the rear that is of slightly larger than the corresponding portion of the first bore 26 and so this is also an interference fit. Thus once the insert has been fully inserted into the first bore 26 it will not slip out under the action of gravity or inertia but needs to be actively withdrawn by a user.

The insert and the sides of the first bore 26 thus define a small passageway 58 therebetween through which fluid may flow. With recess 50 having a diameter of 0.5 mm the passageway 58 has an area and flow rate generally equivalent to a 0.4 mm inside diameter metal cannula. Because of material properties the ratio of flow rate to area changes with materials. Thus fluid in the second bore 24 may flow along the small passageway 58 and exit at the rear end.

The configuration of the remainder of the insert is directed to reduction of material and to aid injection moulding of the insert 40. Accordingly, in cross section, the intermediate portion 42 of the insert is not circular but U shaped with legs 60 defining an opening 62 therebetween. The free ends 64 of the legs 60 engage the surface of the first bore 26 and aid in holding the surface 52 against the bore but the sides 66 do not engage the bore surface. Because this configuration is not essential to the working of the invention it will be understood that other configurations may be used.

Figure 7:
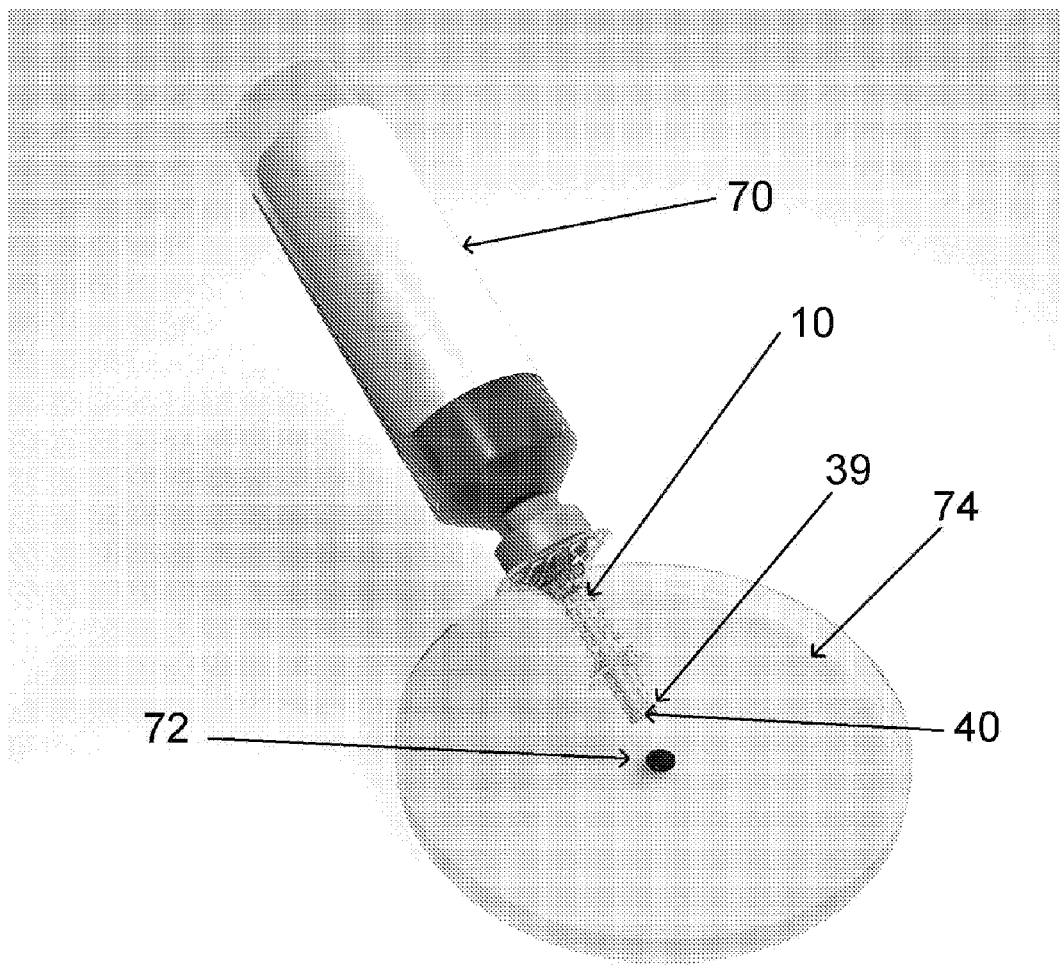
FIG. 7 is a perspective view of the device in use by itself and inserted into a fluid container.

In one use, the cannula 10, with the insert 40 positioned in the first bore 26, is grasped by a user about finger grips 30 and the tip 20 driven through the sealing membrane of a culture bottle 70. The culture bottle 70 and cannula 10 are inverted so the rear end 39 of the cannula 10 is lowermost as seen in FIG. 7. Gravity draws fluid out of the culture bottle, into second bore 24 and subsequently along passageway 58. When the fluid has completely filled the second bore 24 and passageway 58 a drop 72 may be dripped onto test media 74. The small size of the passageway results in small diameter drops. The second bore 24 has a diameter of about 1 mm and the passageway 58 an area equivalent to a diameter of about 0.4 mm so the amount of fluid necessary to fill the second bore 24 and passageway 58 does not significantly reduce pressure in the culture bottle. Thus it is possible to easily obtain the desired number of drops and these drops are relatively consistent in size. Accordingly, the plastic cannula has a performance comparable to a metal needle but without the attendant risk of needle stick injury.

Figure 8:
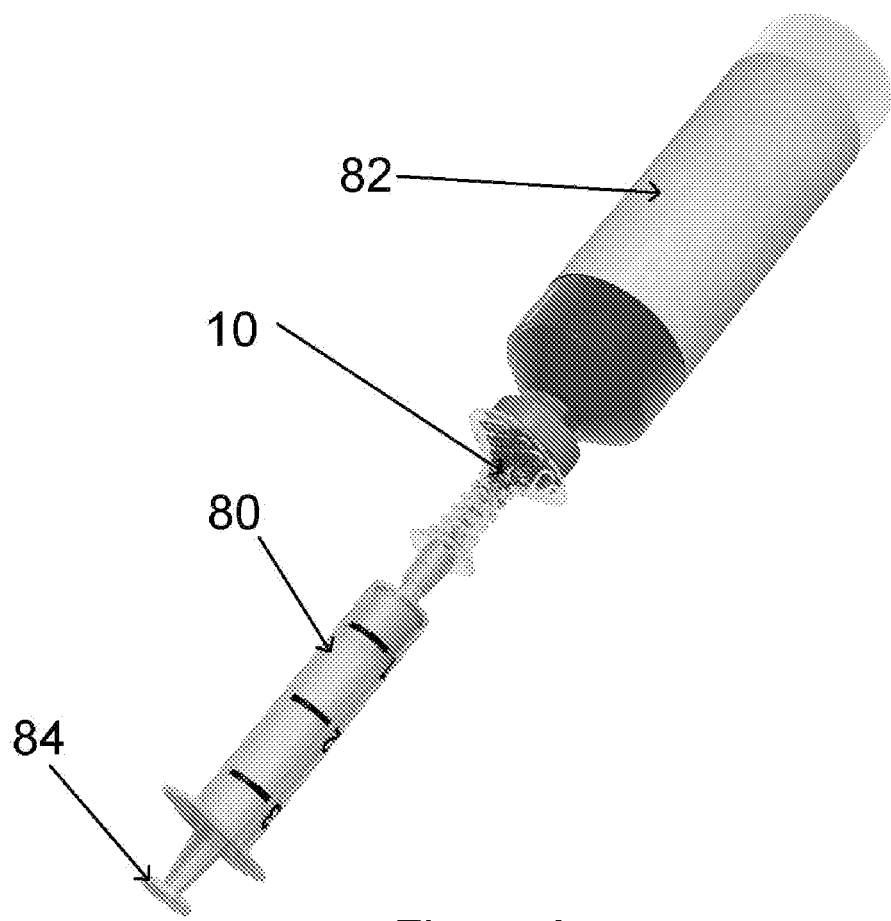
FIG. 8 is a perspective view of the device connected to a syringe and inserted into a fluid container.

The cannula 10 may also be used with a syringe 80, as shown in FIG. 8. The insert 40 is removed by the user grasping the head 46 and pulling outwards, revealing the female luer fitting 34. The male luer fitting of the syringe 80 may be attached and the cannula 10 inserted into the culture bottle 82. As before the culture bottle 82 is inverted and fluid may be withdrawn by withdrawing the syringe plunger 84. Although the first bore 26 is 3.5 mm to 4.2 mm in diameter and so has a significant volume, the ability to apply a significant suction with the syringe means this is does not prevent or significantly limit the desired volume of fluid being withdrawn. If desired, an insert (not shown) that is only as long as the forward portion 36 of the first bore 26 may be inserted, so reducing the effective size of the forward portion 36 whilst leaving the female luer fitting 34 free for connection to the syringe 80.

Unless the context clearly requires otherwise, throughout the description and the claims the words 'comprise', 'comprising', and the like are to be construed in an inclusive sense as opposed to an exclusive or exhaustive sense; that is to say, in the sense of "including, but not limited to".

It will be apparent to those skilled in the art that many obvious modifications and variations may be made to the embodiments described herein without departing from the spirit or scope of the invention.

The claims defining the invention are as follows:

1. A plastics cannula for use in removing samples of fluid from a container sealed with a pierceable membrane, the cannula including
    an elongate body having a front end and a rear end;
    a first bore extending from the rear of the body toward the front end;
    a small diameter needle like portion extending from the front end of the body having a pointed forward end shaped to allow forcible penetration through the membrane and having a second bore therein that extends from the forward end through the front end of the body to be in fluid communication with the first bore;
    the cross-section area of the first bore being significantly greater than that of the second bore, and
    an insert located within the first bore and extending from the front end of the first bore to the rear end to define a passageway from the second bore to the rear of the body, formed between an outer surface of the insert and a surface of the first bore;
    wherein the passageway has a significantly smaller volume than the first bore, and wherein the insert has a longitudinally extending recess that, with a part of the first bore, defines the passageway.

2. The cannula of claim 1 wherein, in cross section, the recess is semicircular.

3. The cannula of claim 1 wherein, in cross section, the recess is semicircular and has a diameter of about 0.5 mm.

4. The cannula of claim 1 wherein the insert has an inner end adjacent the front end of the first bore and the recess extends radially inwards on the inner end surface of the insert.

5. The cannula of claim 1 wherein the passageway has a cross-sectional area which permits a flow rate for fluid equivalent to a metal passageway of about 0.4 mm in inside diameter.

6. The cannula of claim 5 wherein the insert extends out of the rear end of the first bore.

7. The cannula of claim 6 wherein the exposed end of the insert has a head larger than the rear end of the first bore.

8. The cannula of claim 7 wherein the head has a frusto-conical surface that engages the rear end of the bore.

9. The cannula of claim 1 wherein at least part of the first bore has, in cross section, an area equivalent to a circle of diameter in the range of 1 to 10 mm.

10. The cannula of claim 1 wherein at least part of the first bore has, in cross section, an area equivalent to a circle of diameter in the range of 3 to 5 mm.

11. The cannula of claim 1 wherein at least part of the first bore is circular and has a diameter between 3.5 mm and 4.2 mm.

12. The cannula of claim 1 wherein the first bore is between about 15 and 30 mm long.

13. The cannula of claim 1 wherein the first bore is about 26 mm long.

14. The cannula of claim 1 wherein the second bore is between about 15 and 30 mm long.

15. The cannula of claim 1 wherein the second bore is about 20 mm long.

16. The cannula of claim 1 wherein, in cross section, the second bore is circular with an inside diameter of about 1 mm.

17. The cannula of claim 1 wherein at least part of the insert is an interference fit within the first bore.

18. The cannula of claim 1 wherein the second bore is coaxial with the first bore.

19. The cannula of claim 1 wherein at least part of the first bore is frusto-conical, diverging to the rear.

20. The cannula of claim 1 wherein the first bore has a rear portion adapted to receive a male lure fitting.

* * * * *